US010132029B2

(12) United States Patent
Katzenmeier et al.

(10) Patent No.: US 10,132,029 B2
(45) Date of Patent: Nov. 20, 2018

(54) METHOD FOR REDUCING ADHESION OF MICROORGANISMS TO FABRICS

(71) Applicants: SANITIZED AG, Burgdorf (CH); EMPA EIDGENOESSISCHE MATERIALPRUEFUNGS-UND FORSCHUNGSANSTALT, St. Gallen (CH)

(72) Inventors: Heinz Katzenmeier, Luetzelflueh-Goldbach (CH); Peter Stutte, Burgdorf (CH); Sabrina Schmidt-Emrich, Buechen (DE); Linda Thoeny-Meyer, Teufen (CH); Qun Ren Zulian, St. Gallen (CH)

(73) Assignees: SANITIZED AG (CH); EMPA EIDGENOESSISCHE MATERIALPRUEFUNGS-UND FORSCHUNGSANSTALT (CH)

( * ) Notice: Subject to any disclaimer, the term of this patent is extended or adjusted under 35 U.S.C. 154(b) by 285 days.

(21) Appl. No.: 15/104,710

(22) PCT Filed: Dec. 18, 2014

(86) PCT No.: PCT/EP2014/078383
§ 371 (c)(1),
(2) Date: Jun. 15, 2016

(87) PCT Pub. No.: WO2015/091740
PCT Pub. Date: Jun. 25, 2015

(65) Prior Publication Data
US 2016/0319480 A1  Nov. 3, 2016

(30) Foreign Application Priority Data

Dec. 20, 2013  (EP) ..................... 13198710

(51) Int. Cl.
*D06M 13/51* (2006.01)
*D06M 11/77* (2006.01)
(Continued)

(52) U.S. Cl.
CPC ............. *D06M 13/513* (2013.01); *C12Q 1/06* (2013.01); *D06M 10/02* (2013.01); *D06M 16/00* (2013.01);
(Continued)

(58) Field of Classification Search
CPC ........ D06M 13/513; D06M 1/77; A01N 55/10
See application file for complete search history.

(56) References Cited

U.S. PATENT DOCUMENTS 3,769,060 A * 10/1973 Ida ........................ D06M 23/00
427/160
3,860,709 A *  1/1975 Abbott .................. C07F 7/0854
514/63
(Continued)

FOREIGN PATENT DOCUMENTS

JP     H0924089 A    1/1997

OTHER PUBLICATIONS

English Abstract of JP H0924089(A), retrieved from Espace on Sep. 16, 2016.
(Continued)

*Primary Examiner* — Cachet I Sellman
(74) *Attorney, Agent, or Firm* — J.A. Lindeman & Co., PLLC

(57) ABSTRACT

The present invention relates to a method for finishing fibers and/or fabrics, the intention being to reduce the adhesion of microorganisms, especially of bacteria and/or yeasts, to the fibers and/or fabrics. The method involves applying a composition ZS comprising selected hydrophilic silane derivatives to the fibers and/or fabrics. The invention further
(Continued)

relates to a method for the quantitative determination of the adhesion of microorganisms to fibers and/or fabrics.

11 Claims, 1 Drawing Sheet

(51) Int. Cl.
| | |
|---|---|
| *A01N 55/10* | (2006.01) |
| *D06M 13/513* | (2006.01) |
| *D06M 16/00* | (2006.01) |
| *G01N 33/566* | (2006.01) |
| *G01N 33/569* | (2006.01) |
| *C12Q 1/06* | (2006.01) |
| *D06M 10/02* | (2006.01) |

(52) U.S. Cl.
CPC ........ *D06M 16/003* (2013.01); *G01N 33/566* (2013.01); *G01N 33/569* (2013.01); *G01N 2469/00* (2013.01)

(56) References Cited

U.S. PATENT DOCUMENTS

| | | | | |
|---|---|---|---|---|
| 4,404,153 A * | 9/1983 | Gaul, Jr. | ................ | B82Y 30/00 264/29.2 |
| 6,762,172 B1 * | 7/2004 | Elfersy | ................ | A61L 27/34 424/405 |
| 7,404,827 B2 * | 7/2008 | Ishikawa | ................ | C11D 1/72 422/5 |
| 2002/0112293 A1 * | 8/2002 | Trinh | ................ | C11D 3/222 8/115 |
| 2005/0227092 A1 * | 10/2005 | Yamaya | ................ | C09D 5/1625 428/447 |
| 2006/0292345 A1 * | 12/2006 | Dave | ................ | C03C 17/001 428/141 |
| 2007/0212326 A1 * | 9/2007 | Ochs | ................ | A01N 55/00 424/78.27 |
| 2010/0093666 A1 | 4/2010 | Moses | | |
| 2015/0140219 A1 * | 5/2015 | Swamy | ................ | A01N 43/08 427/339 |
| 2015/0322097 A1 * | 11/2015 | Ferritto | ................ | C07F 7/1876 536/56 |

OTHER PUBLICATIONS

English translation of International Preliminary Report on Patentability in corresponding International Application No. PCT/EP2014/078383, dated Jun. 30, 2016.

English translation of International Search Report in corresponding International Application No. PCT/EP2014/078383, dated Aug. 25, 2015.

* cited by examiner

METHOD FOR REDUCING ADHESION OF MICROORGANISMS TO FABRICS

FIELD OF THE INVENTION

The present invention relates to a method for finishing fibers and/or fabrics, the intention being to reduce the adhesion of microorganisms, especially of bacteria and/or yeasts, to the fibers and/or fabrics. The method involves the step of applying a composition ZS comprising selected hydrophilic silane derivatives to the fibers and/or fabrics. The invention further relates to a method for the quantitative determination of the adhesion of microorganisms to fibers and/or fabrics.

BACKGROUND OF THE INVENTION

The majority of fabrics comprise microbiologically degradable material. They are frequently made either wholly or partly of microbiologically degradable fibers, as for example of cotton, cellulose, e.g., viscose, lyocell (e.g., Tencel®), hemp, flax, linen, silk or wool. Fabrics made from synthetic fibers as well, such as from polyester, polyacrylonitrile, polyamide or polypropylene, are regularly colonized by bacteria. Fabrics made from synthetic fibers are colonized especially when they comprise finishing agents, such as softeners, water repellents, antistats and/or binders, for example, or when in the course of their use they pick up microbiologically degradable material, such as organic substances from perspiration or from the environment, for example.

Particularly with synthetic fabrics, as for example with polyester fabrics, it is observed that bacteria adhere to the fabric or fiber and form what is called a biofilm. This biofilm and the bacteria it contains can often not be fully removed on laundering, particularly at the low wash temperatures recommended for polyester fabrics. As a consequence, bacteria remain on the fabric, and may become active when it is worn again and may then result in an increasingly rapid formation of unpleasant odors. This problem brings about an ever greater reduction in the wear time of polyester textiles over the course of time, and often results in an inability for the unpleasant odor of such textiles to be removed completely after a number of wear cycles, in spite of washing. Within technical circles, this phenomenon is well known and is often referred to as "old perspiration odor".

A biofilm is understood in general to be an assembly of microbial cells which are connected to a substrate surface and which are embedded in an extracellular polymeric matrix (e.g., of exo-polysaccharides), which is normally formed by the microbial cells themselves.

The microbial colonization of substrates and the formation of a biofilm normally include the adhesion of microorganisms, especially bacteria, an example being the widespread *Pseudomonas* sp., as a first, critical step. The bacteria or the protein structures of the bacterial envelope adhere to various surfaces usually via unspecific hydrophobic interactions (e.g., Van der Waals' interactions).

Through the release of polymeric substances, especially exo-polysaccharides, over time, the accreted bacteria form a fully-developed biofilm (also referred to as bioslime or slime layer). This biofilm is frequently highly resistant to the use of active antimicrobial ingredients, since the slime layer in general is of low permeability and the microorganisms are embedded in the slime layer. Preventing the initial adhesion of bacteria to surfaces is therefore a preferred approach in the control of bacteria and the prevention of biofilm formation.

An advantage of an antiadhesion coating (often also called an antifouling coating) relative to finishing with active antimicrobial ingredients which directly kill bacteria or inhibit their growth, moreover, is that it is possible to use eco-friendly compounds that are not toxic, such as polymers, for example. It is therefore possible to do largely without the use of biologically active ingredients which are often problematic to humans.

Antifouling coatings for reducing the adhesion of microorganisms to solid substrates have been known for a long time, particularly in the medical sector or as a protective coating for ships. Described in the prior art, for example, are antifouling coatings comprising polyethylene glycol (PEG)-based polymers, as for example in M. Chamley et al. (Reactive & Functional Polymers 71 (2011), 329-334), Kingshott et al. (Langmuir 2003, 19, 6912-6921) or WO 2008/089032.

Document WO 2003/024897 describes a method for coating surfaces, especially hydrophobic surfaces, with specially designed thioethers and amphiphilic thioethers.

Document WO 2008/049108 describes multifunctional biocoatings and methods for employing them. The surface-modifying agent (SMA) may for example comprise dopamine or dopamine derivatives. WO 2008/089032 is directed to an antifouling coating with a modified polyethylene glycol (PEG) polymer, e.g., a dopamine-modified PEG polymer such as PEG-DOHA$_4$.

The publication of Tsibouklis et al. (Contact Angle, Wettability and Adhesion, Vol. 4, 2006, 461-469) describes the formation of biofilms on substrates and compares antifouling coatings made from poly(fluoroalkyl (meth)acrylates) and poly(meth)acrylates.

Document US 2010/0112364 describes a method for coating various substrates, such as metals, fabrics and plastics, where the surface of the substrate is oxidized, after which an unsaturated monomer is applied and polymerized. The coating is said to reduce the adhesion of biological material.

The coating methods described in the prior art are either technically complicated and/or costly in their implementation, and/or yield an antiadhesive coating which lacks adequate effectiveness and stability. In particular, the methods described in the prior art are not capable of providing a stable (especially wash-stable) finish on fibers and/or fabrics that can be applied simply and inexpensively by means of common textile application techniques.

It is critical, moreover, for the development of a coating method of this kind that the antiadhesive activity of the fiber or fabric coating can be determined reliably and rapidly, particularly in a high-throughput process.

Described in the prior art are a multiplicity of methods for the quantitative determination of biofilm formation, and of methods for determining the biomass of an existing biofilm. In the medical sector in particular, such as with implants, the formation of biofilms, by microorganisms of the genus *Staphylococcus*, for example, is critical, since bacteria in a biofilm have fundamentally different properties than suspended bacteria—a greater resistance toward antibiotics, for example.

The publication of Srdjan S. et al. (APMIS, 115: 891-899, 9, 2007) describes the individual steps of a method for the quantitative determination of the formation of biofilm by Staphylococci in various microtiter plates, such as in microtiter plates which have been treated with tissue cultures, for example. A method is described wherein a biofilm is formed on the walls and bases of the microtiter plate and is stained directly in the microtiter plate by means of a suitable dye, such as with crystal violet, for example. The quantity of the accreted dye is evaluated by a suitable technique (e.g., using microtiter plate readers).

The publication of Peeters E. et al. (Journal of Microbiological Methods 72 (2008) 157-165) compares different methods for the quantitative determination of biofilms which have grown in a microtiter plate. One possibility described is that of direct staining in the microtiter plates of biofilms of *P. aesuginaosa* and *S. aureus* with different dyes, e.g., crystal violet, Syto9, and the possibility of evaluation by means of suitable spectroscopic methods.

The publication of Kingshott et al. (Langmuir 2003, 19, 6912-6921) describes a method for determining the adhesion of *Pseudomonas* sp. on modified PET plastics surfaces, where the number of accreted bacteria is determined by indirect conductometry on the basis of the carbon dioxide produced by the accreted bacteria. The publication of Ciag et al. (Langmuir 2012, 28, 1399-1407) describes a bacterial adhesion assay where the bacteria accreted on a PEG-modified surface are stained and examined by means of confocal laser scanning microscopy (CLSM).

The methods of determination described in the prior art are not suitable for fabrics and are often limited to specific microtiter plate systems. The prior-art determination methods often relate to methods in which the biofilm or the number of accreted bacteria is determined directly on the substrate, something which often necessitates a high level of cost and complexity in terms of apparatus and time.

DISCRIPTION OF THE INVENTION

One object of the invention, accordingly, is to provide a new finishing method, more particularly coating method, particularly for fibers and/or fabrics, using nontoxic, environmentally compatible coating agents. The coating is intended to actively reduce the adhesion of microorganisms and to exhibit high stability, particularly wash resistance on fibers and/or fabrics. It is desirable, moreover, for the finishing, more particularly coating, of the fibers and/or fabrics to be able to be carried out simply and inexpensively by means of customary textile finishing techniques.

A further object of the invention is to be able to verify, and reliably quantify, the activity of the coating method, i.e., to provide a method for the quantitative determination of the adhesion of microorganisms to fibers and/or textiles. The determination method ought to be able to be employed reliably and easily for all kinds of fibers and fabrics and for different microorganisms, especially for bacteria and yeasts. It is desirable, moreover, for the method for the quantitative determination of the adhesion of microorganisms to fibers and/or fabrics to be able to be carried out in the form of a high-throughput process.

The present invention relates to a method for finishing fibers and/or fabrics, comprising the steps of
a) providing a composition ZS comprising at least one hydrophilic silane derivative S of the general formula (I)

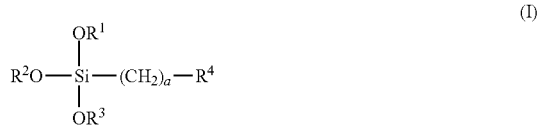

(I)

where
$R^1$, $R^2$ and $R^3$ independently of one another are H or $C_1$-$C_6$ alkyl, preferably methyl or ethyl;
a is an integer from 1 to 10, preferably from 2 to 6, more preferably 3;
$R^4$ is selected from:

i)

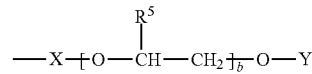

where
X is a bond, $C_{1-12}$ alkylene, $C_{1-12}$ hydroxyalkylene, $C_{1-12}$ haloalkylene, $C_{7-20}$ arylalkylene, —O—T—, —O—T—CH(OH)—, —O—T—CH(OH)—T'—, —O—C(=O)— or —O—C(=O)—T—,
where T and T' independently of one another are selected from $C_{1-12}$ alkylene, $C_{1-12}$ haloalkylene and $C_{1-12}$ hydroxyalkylene, preferably from $C_{1-6}$ alkylene,
$R^5$ is independently at each occurrence H or $C_{1-6}$ alkyl, preferably H or methyl;
Y is H; $C_{1-12}$ alkyl; $C_{1-12}$ hydroxyalkyl, $C_{1-12}$ haloalkyl, $C_{7-20}$ arylalkyl, —C(=O)($C_{1-12}$ alkyl); —$(CH_2)_a$—Si$(OR^1)(OR^2)(OR^3)$, —T—O—$(CH_2)_n$—Si$(OR^1)(OR^2)(OR^3)$;
—T—CH(OH)—O—$(CH_2)_a$—Si$(OR^1)(OR)(OR^3)$, or
—T—CH(OH)—T'—O—$(CH_2)_a$—Si$(OR^1)(OR^2)(OR^3)$ where $R^1$, $R^2$, $R^3$, T, T' and a are as defined above;
b is a number from 0 to 20, preferably 2 to 10;

ii)

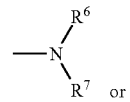

or iii)

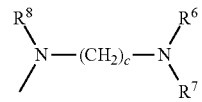

where
$R^6$, $R^7$ and $R^8$ are independently of one another H; $C_{1-12}$ alkyl; $C_{1-12}$ hydroxyalkyl;
$C_{1-12}$ haloalkyl, $C_{7-20}$ arylalkyl; —C(=O)—Z—$R^9$; —C(=O)[OCH($R^{10}$)—$CH_2]_p$—$R^9$; —C(=O)O—Z—$R^9$; —Z—C(=O)[OCH($R^{10}$)—$CH_2]_p$—$R^9$; —Z—[OCH($R^{10}$)—$CH_2]_p$—$R^9$; —Z—$HPO_3^-$ $M^+$; —Z—$SO_3^-M^+$, —Z—COO$^-$ $M^+$, —COO$^-$ $M^+$, —C(=O)—Z—$HPO_3^-M^+$; —C(=O)—Z—$SO_3^-$ $M^+$ or —C(=O)—Z—COO$^-$ M+;
where Z is selected from $C_{1-12}$ alkylene, $C_{1-12}$ haloalkylene and $C_{1-12}$ hydroxyalkylene, Z preferably being $C_{1-6}$ alkylene or $C_{1-6}$ hydroxyalkylene;
$R^9$ is selected from —H, —OH, —O—($C_{1-6}$ alkyl), —$NH_2$, —NH($C_{1-6}$ alkyl) or —N($C_{1-6}$ alkyl)$_2$, preferably selected from —OH and —$NH_2$;
$R^{10}$ independently at each occurrence is selected from H or $C_{1-6}$ alkyl, preferably from H or methyl;

p independently at each occurrence is a number from 1 to 20, preferably from 1 to 10, more preferably from 2 to 7, M is a metal, preferably an alkali metal, more preferably Na;

c is an integer from 1 to 10, preferably from 2 to 5, more preferably 2;

and optionally at least one solvent L;

b) applying the composition ZS to the fibers and/or fabrics;

c) optionally washing and/or drying the fibers and/or fabrics.

With the aid of the method of the invention it is possible for fibers and/or fabrics to be finished with an antiadhesive coating, and for the accretion/adhesion of bacteria to the surface of the fibers and/or fabrics, and the formation of a bacterial film (biofilm), to be effectively prevented.

It has emerged that by means of the method of the invention a particularly stable and wash-resistant finish is possible, which effectively reduces the adhesion of bacteria even after repeated laundering, e.g., 10 to 100 washes, and/or mechanical exposure.

It has been found that it is possible to prevent or significantly reduce the adhesion of a multiplicity of frequently occurring bacteria, such as, for example:

Pseudomonas aeruginosa (*P. aeruginosa*), Escherichia coli (*E. coli*), Staphylococcus aureus (*S. aureus*), Staphylococcus epidermidis (*S. epidermidis*) and Candida albicans (*C. albicans*).

The hydrophilic silane derivatives used are notable, moreover, for their toxicological unobjectionability and for good environmental compatibility.

A particular advantage is that in the case of finishing by the method of the invention, it is possible to do without the use of common active antimicrobial ingredients (e.g., silver salts, thiohydroxamic acid derivatives, isothiazolinone derivatives or benzimidazole derivatives). It has been shown that a coating with the silane derivatives used does not itself exhibit any antimicrobial effect.

An antimicrobial effect is understood in the sense of the present invention to mean that there is a direct interaction with microorganisms, such as bacteria, yeasts and/or viruses, for example, that leads to the killing or to reduced proliferation of the microorganisms.

The method of the invention for finishing fibers and/or fabrics is more particularly a method for antiadhesive finishing, the intention being to reduce or prevent the adhesion (accretion) of microorganisms onto the fibers and/or fabrics.

The microorganisms are, more particularly, bacteria, viruses, fungi, yeasts and algae, more particularly bacteria and yeasts. The microorganisms in question, more particularly bacteria and yeasts in question, are preferably those which typically colonize the skin of humans and of animals.

Fiber (fiber raw material) is understood in the sense of the invention to refer to linear structures which constitute the smallest unit of fabrics or textile materials, it being possible to make distinctions between spun fibers (spinnable fibers, fibers with limited length) and filaments (drawn continuous fibers). Fibers may for example be mineral or vegetable natural fibers, examples being cotton, wool, silk, or synthetic fibers (manmade fibers) produced from synthetic polymers, as for example from polyester or polyamide, or from polymers of natural origin, e.g., regenerated cellulose fibers.

Fabrics are understood in the sense of the invention to be frameworks (structures) of fibers which originate typically from a textile processing operation, the processing operation more particularly comprising spinning, weaving, knitting, and operations modified from and based on them. Fabrics are understood to be semifinished and finished textile products, such as unformed structures, e.g., flocks; linear structures, e.g. filaments, yarns, twists and cables, and sheetlike structures, e.g. wovens, nonwovens and felt fabrics.

A silane derivative in the sense of the present invention is a silicon-organic compound comprising Si—C and Si—O bonds. More particularly in the sense of the invention it is a hydrophilic silane derivative, in which case preferably the radical $R^4$ according to formula I is a hydrophilic radical.

In the sense of the present invention, the stated radicals are defined as follows:

Alkyl designates a univalent radical consisting of a linear, branched or cyclic hydrocarbon group, preferably of a linear or branched hydrocarbon chain, more particularly comprising 1 to 12 carbon atoms. The alkyl radical may for example be methyl, ethyl, n-propyl or isopropyl.

Arylalkyl designates a univalent radical derived from a linear or branched alkyl radical, more particularly comprising 1 to 14 carbon atoms, by the replacement of one or more hydrogen atoms by an aryl group, the aryl group being a substituted or unsubstituted aromatic hydrocarbon group, more particularly comprising 6 carbon atoms. The aromatic hydrocarbon group may for example be phenyl; the arylalkyl radical may for example be a benzyl radical.

Haloalkyl designates the univalent radical derived from a linear or branched alkyl radical, more particularly comprising 1 to 12 carbon atoms, by the replacement of one or more hydrogen atoms by a halogen (—F, —Cl, —Br, —I, more particularly Cl). Halogen designates a substituent selected from fluoride, chloride, bromide or iodide, more particularly chloride. Hydroxyalkyl designates a univalent radical derived from a linear or branched alkyl radical, more particularly comprising 1 to 12 carbon atoms, by the replacement of one or more hydrogen atoms by a hydroxyl group (—OH).

Alkylene, arylalkylene, haloalkylene and hydroxyalkylene designate the corresponding divalent radicals.

The radicals $R^1$, $R^2$ and $R^3$ in formula (I) are selected independently of one another from H or $C_1$-$C_6$ alkyl, preferably from $C_1$-$C_3$ alkyl, more preferably from methyl or ethyl. Especially preferably $R^1$=$R^2$=$R^3$, preferably $R^1$=$R^2$=$R^3$=methyl or ethyl.

One preferred embodiment relates to a method as described above where $R^1$, $R^2$ and $R^3$ independently of one another are methyl or ethyl and a is 3.

The radicals $R^5$ and $R^{10}$ are independently of one another H or $C_{1-6}$ alkyl. The radicals $R^5$ and/or $R^{10}$ are preferably H or $C_{1-3}$ alkyl, especially preferably H, methyl or ethyl, more preferably H or methyl. The orientation of the alkyleneoxy groups —(O—CH($R^5$)—CH$_2$)$_b$ and —(O—CH($R^{10}$)—CH$_2$)$_p$ as per formula (I) may be arbitrary. The skilled person knows that when the corresponding alkylene oxides are incorporated, e.g., propylene oxide and/or butylene oxide, both directions of linkage are possible. The skilled person is also aware that the number of the alkyleneoxy groups, i.e., the indices b and p, are average values.

Index b is a number from 0 to 20, preferably 2 to 15, more preferably from 2 to 10, for example preferably from 9 to 12, for example preferably from 6 to 9, for example preferably from 4 to 6.

Index p is a number from 1 to 20, preferably 1 to 15; more preferably from 2 to 10, for example preferably from 9 to 12, for example preferably from 6 to 9, for example preferably from 4 to 6.

The radical $R^4$ more particularly is a hydrophilic radical, more particularly a radical comprising alkoxy groups, hydroxyl groups, amino groups and/or ionic groups, more particularly anionic groups.

In one preferred embodiment, a hydrophilic silane derivative S of the formula I described above is used where $R^4$ has the structure i)

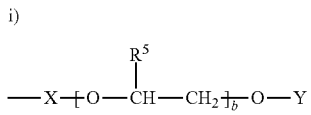

where Y, $R^5$ and b are as defined above and

X is a bond, —O—T—, —O—T—CH(OH)—, —O—T—CH(OH)—T'—, —O—C(=O)— or —O—C(=O)—T—, where T and T' independently of one another are selected from $C_{1-12}$ alkylene, preferably from $C_{1-6}$ alkylene, more preferably from $C_{1-3}$ alkylene, with T and/or T' especially preferably being —CH$_2$—.

In one preferred embodiment the divalent radical X is selected from a bond, —O—(CH$_2$)$_n$—, —O—(CH$_2$)$_n$—CH(OH)—, or —O—(CH$_2$)$_{n'}$—CH(OH)—(CH$_2$)$_n$—, —O—C(=O)—(CH$_2$)$_n$—, where and n and n' independently of one another are an integer from 1 to 6, preferably n=1 and n'=1. More preferably the divalent radical —X— is selected from a bond or —O—CH$_2$—CH(OH)—CH$_2$—.

The orientation of the divalent radical —X— in the group i)

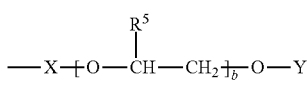

is preferably as indicated (reading direction from left to right), with the left-hand free bond being bonded to the group —(CH$_2$)$_a$— of formula (I) and the right-hand free bond to the group —[O—CH($R^5$)—CH$_2$]$_b$—.

In particular, the above-stated group i) has one of the following structures (i1) to (i7):

(i1)
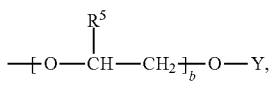

(i2)
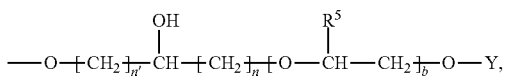

(i3)
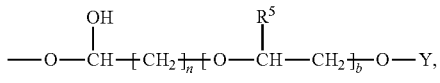

(i4)
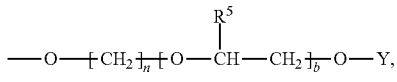

(i5)
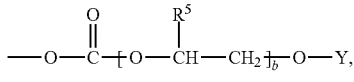

(i6)
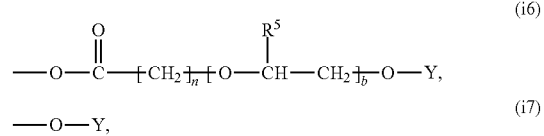

(i7)
—O—Y, where the radicals and indices have the definitions stated above. In the method of the invention for finishing fibers and/or fabrics, preference is given to using a hydrophilic silane derivative S where the above-stated group i) has one of the structures (i1) or (i2).

In one preferred embodiment a hydrophilic silane derivative S of the above-described formula I is used where $R^4$ has the structure ii)

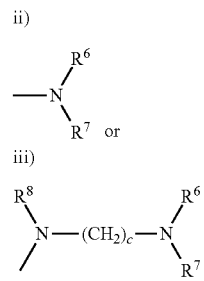

iii)

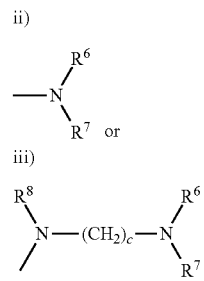

where
$R^6$, $R^7$ and $R^8$ independently of one another are selected from H; $C_{1-12}$ alkyl; $C_{1-12}$ hydroxyalkyl; —C(=O)—Z—$R^9$; —C(=O)[OCH($R^{10}$)—CH$_2$]$_p$—$R^9$; —Z—C(=O)[OCH($R^{10}$)—CH$_2$]$_p$—$R^9$; —Z—[OCH($R^{10}$)—CH$_2$]$_p$—$R^9$; —Z—COO$^-$ M$^+$, —COO$^-$ M$^+$ or —C(=O)—Z—COO$^-$ M$^+$;
where Z is selected from $C_{1-12}$ alkylene or $C_{1-12}$ hydroxyalkylene, preferably from $C_{1-6}$ alkylene or $C_{1-6}$ hydroxyalkylene, more preferably from $C_{1-6}$ alkylene or —(CH(OH))$_s$—CH$_2$— where s=2 to 6, preferably s=3 or 4, $R^9$ is selected from —H, —OH and —NH$_2$,
and where $R^9$, $R^{10}$, c, p and M are as defined above.

In one preferred embodiment at least one of the radicals $R^6$, $R^7$ and $R^8$, preferably precisely two of the radicals, preferably precisely one of the radicals, is H and the other radical or the other radicals is or are an above-stated group that is not H.

In one preferred embodiment Z is a divalent radical —(CH$_2$)$_m$— where m is 1 to 6, preferably 1 to 3. In one preferred embodiment Z is a branched alkylene group having 2 to 6 carbon atoms, Z preferably being a divalent radical —CH(CH$_3$)—CH$_2$— or —CH$_2$—CH(CH$_3$)—.

In one preferred embodiment the radical Z is $C_{1-12}$ hydroxyalkylene, preferably $C_{1-6}$ hydroxyalkylene. More particularly Z may be a hydroxyalkylene group —(CH(OH))$_s$—CH$_2$— where s=2 to 6, preferably s=3 or 4, especially preferably 4. More particularly, therefore, at least one of the radicals $R^6$, $R^7$ and $R^8$ is —C(=O)—Z—$R^9$, where Z is a divalent radical —(CH(OH))$_s$—CH$_2$— where s=2 to 6, preferably s=3 or 4, especially preferably s=4, and $R^9$ is —OH. More particularly, —C(=O)—Z—$R^9$ may be a radical derived from a C6 or C5 saccharide, preferably from a C6 saccharide, as for example from glucose, mannose, ribose, fructose or galactose.

One preferred embodiment uses a hydrophilic silane derivative S of the above-described formula I where $R^4$ is a group described under ii) or iii), with the proviso that at least one of the radicals $R^6$, $R^7$ and $R^8$ contains at least one anionic group.

Preference is given to using a hydrophilic silane derivative S of the above-described formula I where at least one of the radicals $R^6$, $R^7$ and $R^8$ contains at least one anionic group selected from carboxylate (—COO$^-$), sulfonate (—SO$_3^-$) and phosphonate (—PO$_3^{2-}$, —HPO$_3^-$). The statement of the group —HPO$_3^-$ M$^+$ here is intended to encompass the groups —PO$_3^{2-}$ and —HPO$_3^-$ with appropriate compensation of the anionic charge by a monovalent and/or divalent metal ion M$^+$ and/or M$^{2+}$. The skilled person is aware that the stated anionic groups may be present in protonated or partly protonated form depending on the conditions (e.g., pH). More particularly the metal ion M$^+$ is an alkali metal ion and/or an alkaline earth metal ion, more particularly an alkali metal ion, more particularly Na$^+$.

Preferably, therefore, at least one of the radicals $R^6$, $R^7$ and $R^8$ may be a radical selected from —Z—HPO$_3^-$M$^+$; —Z—SO$_3^-$M$^+$, —Z—COO$^-$ M$^+$, —COO$^-$ M$^+$, —C(=O)—Z—HPO$_3^-$ M$^+$; —C(=O)—Z—SO$_3^-$M$^+$, —C(=O)—Z—COO$^-$ M$^+$, where the radicals and indices are as defined above. Especially preferably at least one of the radicals $R^6$, $R^7$ and $R^8$ is a radical selected from —Z—COO$^-$ M$^+$, —COO$^-$ M+ and —C(=O)—Z—COO$^-$ M$^+$.

The invention relates more particularly to a method described above where $R^4$ is a group selected from:

 (x)

where b and Y are as defined above; preferably where b=2 to 20 and Y is selected from H and $C_1$-$C_6$ alkyl, preferably from H, methyl and ethyl;

—O—Y (xi)

where Y is as defined above; preferably where Y is selected from H, $C_{1-6}$ alkyl and —C(=O)($C_{1-12}$ alkyl), preferably from H, methyl, ethyl and acetyl;

 (xii)

where $R^1$, $R^2$, $R^3$, a and b are as defined above; preferably where a=2 to 6, preferably 3, preferably where b=2 to 10; preferably $R^1$, $R^2$ and $R^3$ independently of one another are methyl or ethyl;

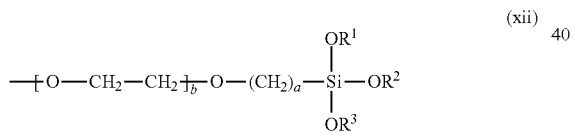 (xiii)

where $R^1$, $R^2$, $R^3$, a and b are as defined above; preferably where a=2 to 6, preferably 3, preferably where b=2 to 20, preferably 5 to 10, and $R^1$, $R^2$ and $R^3$ are preferably independently of one another methyl or ethyl;

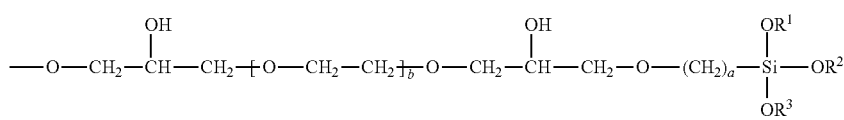 (xiv)

where Z and $R^9$ are as defined above; preferably where Z is selected from $C_{1-12}$ alkylene or $C_{1-12}$ hydroxyalkylene, preferably from $C_{1-6}$ alkylene or $C_{1-6}$ hydroxyalkylene; preferably where $R^9$ is selected from —H, —OH and —NH$_2$; preferably from —H and —OH; preferably $R^9$ is OH;

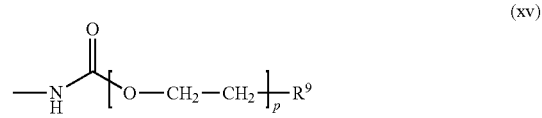 (xv)

where p and $R^9$ are as defined above; preferably where p=1 to 20, preferably 1 to 10, more preferably 4 to 6; and $R^9$ is preferably selected from —OH, —OCH$_3$, —OCH$_2$CH$_3$ and —NH$_2$, preferably from —OH and —NH$_2$;

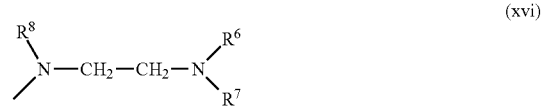 (xvi)

where $R^6$, $R^7$ and $R^8$ are as defined above; preferably where $R^6$, $R^7$ and $R^8$ are selected independently of one another from —Z—HPO$_3^-$M$^+$; —Z—SO$_3^-$M$^+$, —Z—COO$^-$ M$^+$, —COO$^-$ M$^+$, —C(=O)—Z—HPO$_3^-$M+; —C(=O)—Z—SO$_3^-$M$^+$, —C(=O)—Z—COO$^-$ M$^+$, more preferably selected from —Z—COO$^-$ M$^+$, —COO$^-$ M$^+$ and —C(=O)—Z—COO$^-$ M+, where Z is selected from $C_{1-12}$ alkylene, preferably from $C_{1-6}$ alkylene;

 (xvii)

where t is a number from 1 to 6, preferably 1 to 3, especially preferably 2.

In one preferred embodiment of the invention, radical $R^4$ is a group (xiv).

The radical $R^4$ as per (xiv) is preferably a radical of the following formula

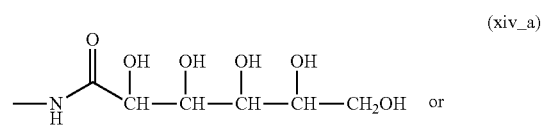 (xiv_a)

-continued

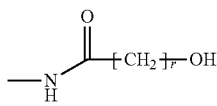
(xiv_b)

where r is a number from 1 to 6, preferably 1 to 3, especially preferably 3.

The radical $R^4$ as per (xvi) is preferably a radical of the following formula

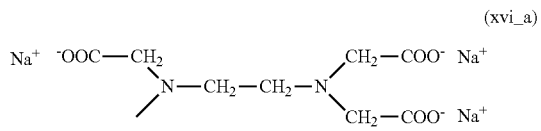
(xvi_a)

Preference is given to using at least one of the following compounds of the formulae (S1a) to (S5a) as hydrophilic silane derivative S:

In one preferred embodiment at least one compound of the formula (S3a) is used as hydrophilic silane derivative S.

Preferably the group —C(=O)—Z—$R^9$ in formula (S4a) is a group —C(=O)—Z—$R^9$, where Z is —(CH(OH))$_s$—CH$_2$— where s=2 to 6, preferably s=3 or 4, especially preferably s=4, and $R^9$ is —OH. More particularly, —C(=O)—Z—$R^9$ in the formula (S4a) may be a radical derived from a $C_6$ or $C_5$ saccharide, preferably from a $C_6$ saccharide, as for example from glucose, mannose, ribose, fructose or galactose.

Preferably at least one of the radicals $R^6$, $R^7$ and $R^8$, preferably all radicals $R^6$, $R^7$ and $R^8$, in formula (S5a) are a radical containing at least one anionic group selected from carboxylate (—COO$^-$), sulfonate (—SO$_3^-$) and phosphonate (—PO$_3^{2-}$, —HPO$_3^-$). Preferably, therefore, at least one of the radicals $R^6$, $R^7$ and $R^8$ in formula (S5a) may be a radical selected from —Z—HPO$_3^-$M$^+$; —Z—SO$_3^-$M$^+$, —Z—COO$^-$ M$^+$, —COO$^-$ M$^+$, —C(=O)—Z—HPO$_3^-$M$^+$; —C(=O)—Z—SO$_3^-$M$^+$, —C(=O)—Z—COO$^-$ M$^+$, where the radicals and indices are as defined above. Especially preferably at least one of the radicals $R^6$, $R^7$ and $R^8$ in

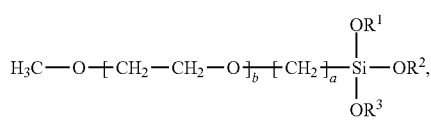
(S1a)

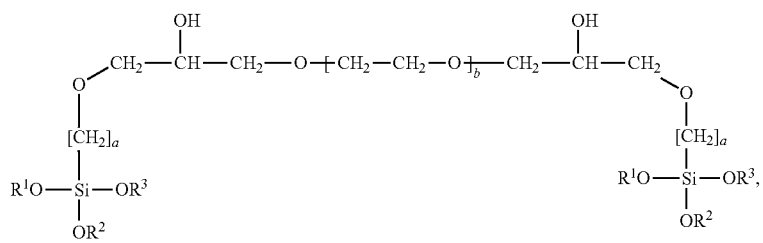
(S2a)

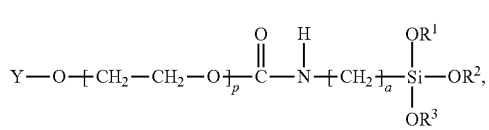
(S3a)

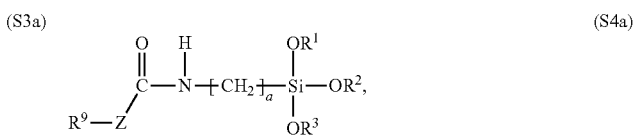
(S4a)

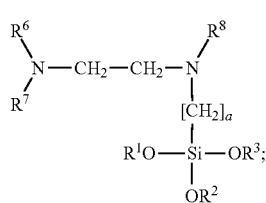
(S5a)

where the radicals and indices have the definitions stated above. In particular, the preferred embodiments stated above for the radicals and indices are valid for the compounds of the formulae (S1a) to (S5a).

formula (S5a) is a radical selected from —Z—COO$^-$ M$^+$, —COO$^-$ M$^+$ and —C(=O)—Z—COO$^-$ M$^+$.

Preference is given to using at least one of the following compounds (S1) to (S11) as hydrophilic silane derivative S:

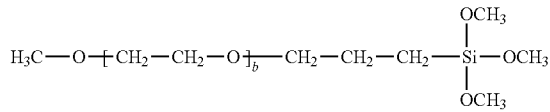
(S1)
where b = 0-20, preferably b = 5-10
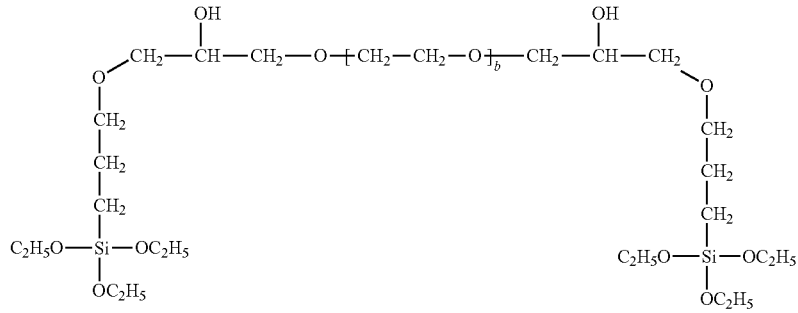
(S2)
where b = 0-20, preferably b = 5-10
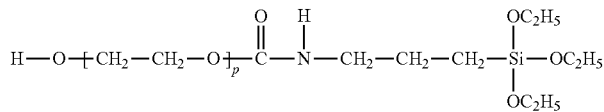
(S3)
where p = 1-20, preferably p = 4-6
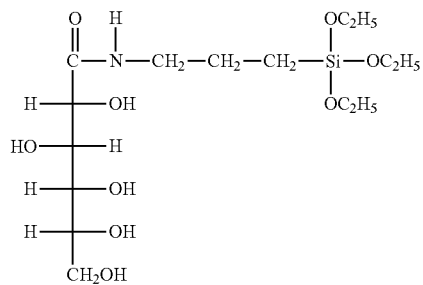
(S4)
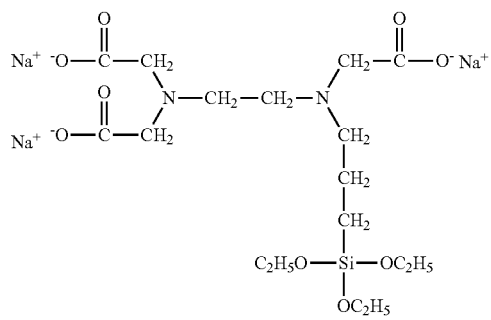
(S5)
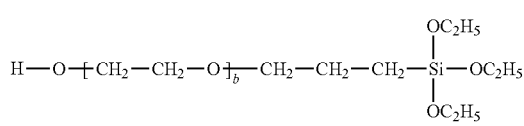
(S6)
where b = 1 to 20, preferably b = 6-9
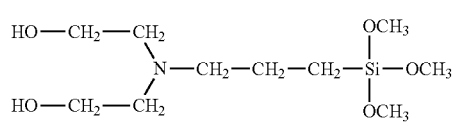
(S7)
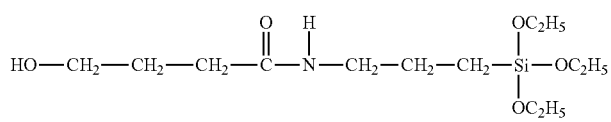
(S8)
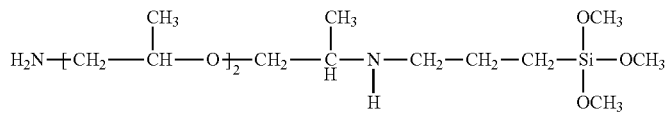
(S9)
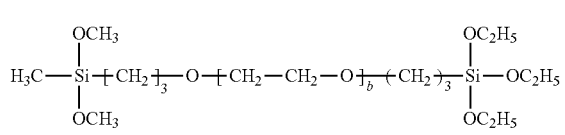
(S10)
where b = 1 to 20, preferably b = 6-9

(S11)

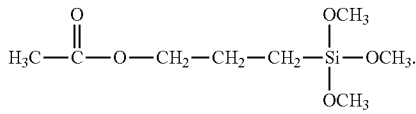

The invention relates preferably to a method for finishing fibers and/or fabrics where the composition ZS comprises at least one hydrophilic silane derivative S selected from the compounds S1 to S5.

In one particularly preferred embodiment, the invention relates to a method for finishing fibers and/or fabrics where the composition ZS comprises at least one hydrophilic silane derivative S3; more particularly, the composition ZS may comprise exclusively S3 as hydrophilic silane derivative.

The method of the invention encompasses the providing of the composition ZS comprising an above-described hydrophilic silane derivative S of the formula (I) and optionally at least one solvent L. The composition ZS preferably consists of at least one above-described hydrophilic silane derivative S of the formula (I) and at least one solvent L.

In the method of the invention, a composition ZS is preferably used which comprises 0.00001 to 100 wt %, preferably 0.0001 to 10 wt %, more preferably 0.001 to 5 wt %, especially preferably 0.01 to 1 wt %, with further preference 0.001 to 0.1 wt %, of the at least one hydrophilic silane derivative S, based on the overall composition ZS.

In the method of the invention, preferably, the at least one hydrophilic silane derivative S is applied at a concentration (application concentration) of 0.00001 to 5 wt %, preferably of 0.0001 to 2 wt %, preferably of 0.001 to 0.1 wt %, to the fibers and/or fabrics, based on the total weight of the fibers and/or fabrics.

The composition ZS preferably comprises a solvent L selected from water, polar organic solvents, nonpolar organic solvents, and mixtures thereof. Employed as organic solvents L in particular may be known solvents which are not easily or highly flammable, are not toxic, and can be mixed with water in the required concentration range. For example, the solvent L may comprise (or consist of) water, mono- or polyhydric $C_{1-6}$ alcohols, glycol, glycol derivatives, polyglycols, polyglycol ethers, ethers and mixtures thereof.

In one preferred embodiment the composition ZS comprises at least one solvent L selected from the group consisting of water, methyl triglycol, ethylene glycol, polyethylene glycol, propylene glycol, polypropylene glycol, propylene glycol monomethyl ether, propylene glycol dimethyl ether, propylene glycol monoethyl ether, propylene glycol diethyl ether, methanol, ethanol, propanol and butanol. More particularly the solvent comprises (or consists of) methylene triglycol (triethylene glycol monomethyl ether) or a mixture of methylene triglycol and water.

The composition ZS comprises the at least one solvent L preferably in an amount of 0 to 99.99999 wt %, preferably in an amount of 90 to 99.99 wt %, more particularly in an amount in the range from 95 to 99.9 wt %, based on the composition ZS.

The composition ZS preferably comprises the following components (or consists of them):
0.0001 to 100 wt %, preferably 0.0001 to 10 wt %, preferably 0.001 to 5 wt %, more preferably 0.01 to 2 wt %, especially preferably 0.01 to 1 wt %, of the at least one hydrophilic silane derivative S;
0 to 99.9999 wt %, preferably 90 to 99.9999 wt %, preferably 95 to 99.999 wt %, more preferably 98 to 99.99 wt %, especially preferably 99 to 99.99 wt %, of the at least one solvent L.

The above-described composition ZS may optionally comprise 0 to 10 wt %, preferably 0 to 1 wt %, more preferably 0.0001 to 0.1 wt %, based on the overall composition ZS, of at least one further additive A. The at least one further additive A may typically be selected from known textile assistants. For example, the at least one additive A may comprise pH buffers, such as sodium acetate or an acid, formic acid or acetic acid for example, softeners, water repellents, oil repellents, binders, crosslinkers, flame retardants, fabric dyes, sewability improvers and/or soil repellents.

Also possible is the use of an active antimicrobial ingredient as further additive A, as typically used in the antimicrobial finishing of fibers and textiles, examples being antimicrobial compounds having quaternary ammonium functions (e.g., dimethyltetradecyl-3-(trimethoxysilyl)propylammonium chloride or dimethyloctadecyl-3-(trimethoxysilyl)propylammonium chloride); silver salts and silver derivatives, thiohydroxamic acid derivative (e.g., pyrithiones, such as sodium pyrithione or zinc pyrithione), isothiazolinone derivatives (e.g., 1,2-benzisothiazolin-3-one (BIT), octylisothiazolin-3-one (OIT) and methylisothiazolin-3-one (MIT), 4,5-dichloro-2-n-octyl-4-isothiazolin-3-one (DCOIT), butyl-1,2-benzisothiazolin-3-one (BBIT)) or benzimidazole derivatives (e.g., 2-(4-thiazolyl)-1H-benzimidazole). In one preferred embodiment the composition ZS contains no active antimicrobial ingredient.

The composition ZS more particularly comprises the following components (or consists of them):
0.0001 to 10 wt %, preferably 0.001 to 5 wt %, more preferably 0.01 to 2 wt %, especially preferably 0.01 to 1 wt %,
of the at least one hydrophilic silane derivative S;
90 to 99.9999 wt %, preferably 95 to 99.999 wt %, more preferably 98 to 99.99 wt %, especially preferably 99 to 99.99 wt %, of the at least one solvent L as described above, preferably selected from the group consisting of water, methyl triglycol, ethylene glycol, polyethylene glycol, propylene glycol, polypropylene glycol, propylene glycol monomethyl ether, propylene glycol dimethyl ether, propylene glycol monoethyl ether, propylene glycol diethyl ether, methanol, ethanol, propanol and butanol, more preferably methylene triglycol;
0 to 10 wt %, preferably 0 to 1 wt %, more preferably 0.0001 to 0.1 wt % of the at least one further additive A.

Unless otherwise indicated, the figures in wt % are based in each case on the total amount of the composition ZS. For the purposes of the present invention, the datum ppm refers to mg/kg.

The composition ZS can be applied to the fibers and/or fabrics with the aid of a known method for the finishing of fibers or fabrics. The application of the composition ZS in step b takes place preferably by means of padding methods;

foam application; spray methods, more particularly spray application; coating, more particularly doctor blade methods, or an exhaust method, preferably by means of padding methods or an exhaust method.

It is possible, moreover, for the composition ZS of the invention to be applied to the fibers and/or fabrics in connection with a laundering and/or cleaning step, as for example in the course of a customary domestic wash in a washing machine.

The method of the invention may optionally comprise as step c) the washing and/or drying of the fibers and/or fabrics. This may be done by means of the common methods known to the skilled person,—for example, directly after finishing with the hydrophilic silane derivative S.

The method of the invention can be used for finishing of fibers and/or fabrics of virtually any kind, as for example of fibers and/or fabrics which comprise synthetic and/or natural fibers, such as cotton; regenerated cellulose, e.g., viscose, lyocell (e.g., Tencel®); hemp; flax; linen; silk, wool, polyester, polyamide and polyethylene. Preferred are those fibers and/or fabrics which consist substantially of cotton, regenerated cellulose, silk, wool, polyester and/or polyamide. Good results have also been obtained with fibers and/or fabrics which comprise synthetic materials or which consist of synthetic materials. Examples include fibers and/or fabrics of polyamide and/or polyester. The fabrics finished by means of the method of the invention may preferably be woven goods, knitted goods, nonwovens or yarns, although other fabrics may also be finished. The fabrics more particularly are textile products of the clothing industry (e.g., ladies outerwear, menswear, childrenswear, sport and leisure apparel, workwear, socks, stockings and underwear), bedding (e.g., bed covering and sheets), mattress materials, home furnishings, seat covers, upholstery fabrics, textiles for footwear, shower curtains, filters, carpets, protective articles (e.g., masks and bandages) and the like.

In one preferred embodiment the invention relates to a method as described above for finishing fibers and/or fabrics where the fibers and/or fabrics in question are those which comprise synthetic fibers, more particularly fibers of polyester, and/or polyamide. In one preferred embodiment the invention relates to a method described above for finishing fibers and/or fabrics where the fibers and/or fabrics in question are those which consist substantially of synthetic fibers, more particularly fibers of polyester and/or polyamide. With more particular preference the fibers and/or fabrics are sport and leisure apparel consisting substantially of synthetic fibers, more particularly fibers of polyester and/or polyamide.

The invention also relates to the fibers and/or fabrics furnished with a hydrophilic silane derivative S, produced according to the finishing method of the invention. The individual components, such as particularly hydrophilic silane derivative S, fibers and/or fabrics, and further additives, are subject to the preferred embodiments identified above—in connection with the finishing method of the invention.

A further subject of the invention concerns the use of a hydrophilic silane derivative S of the general formula (I) as described above for reducing the accretion of microorganisms onto a solid substrate. The individual components, such as particularly silane derivative S, fibers and/or fabrics, and further additives, are subject to the preferred embodiments identified above—in connection with the finishing method of the invention.

Preferably the invention relates to the use of a hydrophilic silane derivative S of the general formula (I) as described above for reducing the accretion of microorganisms onto a solid substrate where the solid substrate in question is a substrate selected from glass, ceramic, plastic, metal, fibers and fabrics, more particularly selected from glass, fibers and fabrics.

In one preferred embodiment the solid substrate is a substrate selected from glass, ceramic, plastic and metal, more particularly glass and/or plastic, preferably glass.

The invention preferably relates to the use of a hydrophilic silane derivative S of the general formula (I) for reducing the accretion of microorganisms onto a solid substrate selected from glass, ceramic, plastic and metal, preferably glass, where $R^4$ is a group ii) 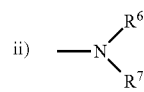

where
$R^6$ and $R^7$ independently of one another are H; $C_{1-12}$ alkyl; $C_{1-12}$ hydroxyalkyl;
—C(=O)—Z—$R^9$; —C(=O)[OCH($R^{10}$)—CH$_2$]$_p$—$R^9$; —C(=O)O—Z—$R^9$; —Z—C(=O)[OCH($R^{10}$)—CH$_2$]$_p$—$R^9$; —Z—[OCH($R^{10}$)—CH$_2$]$_p$—$R^9$; —Z—HPO$_3^-$ M$^+$; —Z—SO$_3^-$M$^+$, —Z—COO$^-$ M$^+$, —COO$^-$ M$^+$, —C(=O)—Z—HPO$_3^-$M$^+$; —C(=O)—Z—SO$_3^-$M$^+$ or —C(=O)—Z—COO$^-$ M$^+$;

where Z is selected from $C_{1-12}$ alkylene, $C_{1-12}$ haloalkylene, $C_{1-12}$ hydroxyalkylene, Z preferably being $C_{1-6}$ alkylene or $C_{1-6}$ hydroxyalkylene;
$R^9$ is selected from —H, —OH, —O—($C_{1-6}$ alkyl), —NH$_2$, —NH($C_{1-6}$ alkyl) or —N($C_{1-6}$ alkyl)$_2$, preferably selected from —OH and —NH$_2$;
$R^{10}$ independently at each occurrence is selected from H or $C_1$-$C_6$ alkyl, preferably H or methyl;
p independently at each occurrence is a number from 1 to 20, preferably from 1 to 10, more preferably from 2 to 7,
M is a metal, preferably an alkali metal, more preferably Na.

Preferably $R^6$ and $R^7$ independently of one another are H or C(=O)—Z—$R^9$, where Z is selected from $C_{1-12}$ alkylene and $C_{1-12}$ hydroxyalkylene, preferably from $C_{1-6}$ alkylene and $C_{1-6}$ hydroxyalkylene; and $R^9$ is selected from —H and —OH.

The invention preferably relates to the use of a hydrophilic silane derivative S selected from the above-described compounds S1 to S11 for reducing the accretion of microorganisms onto a solid substrate.

The invention preferably relates to the use of a hydrophilic silane derivative S of the general formula (I) for reducing the accretion of microorganisms onto a solid substrate selected from glass, ceramic, plastic and metal, preferably glass, where $R^4$ is a group selected from (xiv)

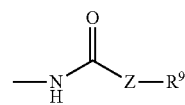

where Z and R⁹ are as defined above, preferably where Z is selected from $C_{1-12}$ alkylene or $C_{1-12}$ hydroxyalkylene, preferably from $C_{1-6}$ alkylene or $C_{1-6}$ hydroxyalkylene, and R⁹ is selected from —H, —OH and —NH₂, preferably from —H and —OH, R⁹ preferably being —OH.

Preferably R⁴ is

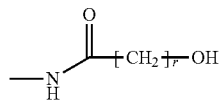 (xiv_b)

where r is a number from 1 to 6, preferably 1 to 3, especially preferably 3.

The invention preferably relates to the use of a hydrophilic silane derivative S selected from the above-described compounds S1 to S11, preferably selected from the compounds S1, S2, S4 and S8, especially preferably S4 and/or S8, for reducing the accretion of microorganisms onto a solid substrate selected from glass, ceramic, plastic and metal, preferably glass.

The invention preferably relates to the use of a hydrophilic silane derivative S selected from the above-described compounds S1 and S3, preferably S3, for reducing the accretion of microorganisms onto a solid substrate selected from glass, ceramic, plastic and metal, preferably glass.

The invention relates more particularly to the use of a hydrophilic silane derivative S of the general formula (I), as described above, for reducing the accretion of microorganisms onto a solid substrate, where the solid substrate is coated with a composition comprising at least one hydrophilic silane derivative S of the general formula (I), as described above. More particularly in this case the solid substrate is coated with a composition comprising at least one hydrophilic silane derivative S and at least one solvent. As solvent L it is possible in particular to use the solvents described above in connection with the finishing method of the invention. For the coating of a solid substrate it is possible more particularly to use an organic mono-, di- or polyalcohol and/or water, preference being given to using $C_{1-6}$ monoalcohols and/or water, and particular preference to using water, ethanol, methanol or mixtures thereof.

The solid substrate can be coated more particularly using a composition which comprises 0.00001 to 100 wt %, preferably 0.001 to 10 wt %, especially preferably 0.01 to 5 wt % of the hydrophilic silane derivative S.

The invention relates more particularly to the use of a composition which comprises a hydrophilic silane derivative S as described above and at least one solvent for reducing the accretion of microorganisms onto a solid substrate.

The microorganisms may more particularly be bacteria, viruses, fungi, yeasts and algae. Preferably they are Gram-positive and Gram-negative bacteria or yeasts which occur typically on the human skin, examples being microorganisms of the genus *Pseudomonas, Escherichia, Staphylococcus* and *Candida*. The microorganisms are preferably microorganisms selected from representatives of the following genera:

*Alternaria*, such as *Alternaria alternata*; *Aspergillus*, such as *Aspergillus niger, Aspergillus repens*; *Aureobasidium*, such as *Aureobasidium pullulans*; *Chaetomium*, such as *Chaetomium globosum*; *Coniophora*, such as *Coniophora puteana*; *Cladosporium*, such as *Cladosporium cladosporoides*; *Candida*, such as *Candida albicans*; *Lentinus*, such as *Lentinus tigrinus*; *Penicillium*, such as *Penicillium funiculosum*; *Rhodotorula*, such as *Rhodotorula rubra*; *Sclerophoma*, such as *Sclerophoma pityophila*; *Trichoderma*, such as *Trichoderma viride*; *Ulocladium*, such as *Ulocladium atrum*; *Escherichia*, such as *Escherichia coli*; *Pseudomonas*, such as *Pseudomonas aeruginosa*; *Staphylococcus*, such as *Staphylococcus aureus* or *Staphylococcus epidermidis*, preferably selected from representatives of the genera *Candida, Escherichia, Pseudomonas* and *Staphylococcus*, more preferably selected from representatives of the genera *Pseudomonas* and *Staphylococcus*.

The microorganisms are more particularly bacteria or yeasts selected from the group consisting of *Pseudomonas aeruginosa* (*P. aeruginosa*), *Escherichia coli* (*E. coli*), *Staphylococcus aureus* (*S. aureus*), *Staphylococcus epidermidis* (*S. epidermidis*) and *Candida albicans* (*C. albicans*), especially preferably from *Pseudomonas aeruginosa* (*P. aeruginosa*) and *Staphylococcus aureus* (*S. aureus*).

A further subject of the invention concerns a method for the quantitative determination of the accretion (adhesion) of microorganisms onto a solid substrate selected from fibers and/or fabrics, comprising the following steps:

a') preparing an aqueous suspension comprising one or more different microorganisms;

b') contacting the aqueous suspension comprising one or more different microorganisms with the solid substrate, preferably at a temperature in the range from 10 to 50° C. and over a period from 0.5 to 10 h;

c') separating the solid substrate F from the supernatant suspension and washing the substrate;

d') removing the accreted microorganisms from the solid substrate by exposure to shearing and/or ultrasound and/or enzymes;

e') determining the amount of microorganisms removed.

The determination method of the invention makes it possible in particular to determine the amount of adhered microorganisms on fibers and/or fabrics, this adhesion often representing the first step in the formation of an unwanted biofilm. In particular it is not necessary for a complete biofilm to be formed and determined. With the determination method of the invention, in particular, it is primarily the first critical step in biofilm formation, namely the adhesion (accretion) of the microorganisms on the fiber and/or fabric surface, that is determined. A particular feature of the determination method of the invention is that the contacting of the fibers and/or fabrics with the microorganisms occurs over a relatively short period of time, preferably 1 to 10 h, and in a medium which does not require, or does not enable, the growth of the microorganisms (as a result of lack of nutrients, for example).

It has surprisingly emerged that by means of the determination method of the invention, it is possible for the tendency of fibers and/or fabrics to attract adhering bacteria to be determined reliably, safely and rapidly. The determination method of the invention is especially suitable for determining the quality and efficacy of an antiadhesive coating on fibers and/or fabrics. The method of the invention can in particular be carried out in one or more microtiter plates and is suitable for being implemented in the form of a high-throughput process, such as a high-throughput screening process, for example.

Because the complete formation of a biofilm is not necessary with the determination method of the invention, there is no need for the laborious washing of the biofilm, in which typically different amounts of the slime layer are washed off, something which may lead to errors, for example, in the context of staining with fluorescent dye and the subsequent fluorescence measurement. A further advantage is that there is no need for the use of nutrient solution, thereby making the subsequent fluorescence determination more reliable.

The determination method of the invention is notable in particular for the fact that it represents a simple and reliable method for determination, for example, of the efficacy of an antiadhesive coating on fibers and/or fabrics.

The method of the invention for quantitative determination of bacterial adhesion comprises the preparing of an aqueous suspension comprising one or more different microorganisms (step a').

The aqueous suspension comprising one or more different microorganisms is prepared preferably by suspending of a defined amount of a bacterial culture, as for example an overnight culture, in an aqueous medium. The aqueous medium of the suspension preferably is sterile and contains no nutrients (non-nutrient medium).

Preferably it is a suspension comprising one or more different microorganisms and an aqueous medium. More particularly the aqueous medium is free from nutrients, more particularly from nutrients which promote and/or enable the growth of microorganisms. The aqueous medium is preferably free from nutrients which constitute a carbon source, examples being carbohydrates, proteins, and amino acids.

The aqueous medium is preferably an aqueous (more particularly sterile) solution comprising at least one salt selected in particular from sodium chloride, potassium chloride, sodium hydrogenphosphate, disodium hydrogenphosphate, potassium dihydrogenphosphate, and dipotassium hydrogenphosphate. The aqueous medium preferably is an isotonic aqueous solution comprising at least one of the salts stated above.

More particularly the aqueous medium comprises at least one of the above-stated salts at a concentration such that the solution has an osmotic pressure which corresponds to the osmotic pressure in the cells of the human body, such as of the blood plasma, for example (isotonic solution). More preferably the aqueous medium is sterile, isotonic (physiological) saline solution (0.9 wt % strength sodium chloride solution), phosphate-buffered saline solution (PBS buffer) or distilled/deionized water, especially preferably isotonic saline solution.

The suspension in question is preferably a suspension consisting of one or more different microorganisms and an aqueous medium as described above. Preferably it is a suspension consisting of one or more different microorganisms and an aqueous medium, with the aqueous medium constituting a sterile, aqueous solution of at least one of the above-stated salts.

The aqueous suspension preferably comprises at least one of the above-stated microorganisms, selected more particularly from bacteria and yeasts.

The aqueous suspension preferably comprises one or more microorganisms selected from the group consisting of *Pseudomonas aeruginosa* (*P. aeruginosa*), *Escherichia coli* (*E. coli*), *Staphylococcus aureus* (*S. aureus*), *Staphylococcus epidermidis* (*S. epidermidis*) and *Candida albicans* (*C. albicans*), especially preferably from *Pseudomonas aeruginosa* (*P. aeruginosa*) and *Staphylococcus aureus* (*S. aureus*). In one preferred embodiment the aqueous suspension comprises exclusively one kind of microorganism, more particularly exclusively one of the above-stated microorganisms.

The aqueous suspension comprising one or more different microorganisms is prepared in step a') in particular by centrifuging the cells of an overnight culture of the microorganism, carrying out washing with an aqueous medium described above, preferably with isotonic (physiological) saline solution, and carrying out suspension in an aqueous medium described above, preferably in isotonic saline solution.

The aqueous suspension in step a') comprising one or more different microorganisms preferably has an optical density, typically measured at 595 nm, in the range from 0.8 to 1.5; preferably from 1 to 1.5; especially preferably from 1 to 1.3; for example, about 1.2. The optical density of the aqueous suspension is typically adjusted to the desired figure in step a') by centrifuging an overnight microorganism culture, taking up the microorganism in an aqueous medium, and performing one or more dilution steps.

The method of the invention for quantitative determination of bacterial adhesion comprises the contacting of the aqueous suspension comprising one or more different microorganisms with the solid substrate (step b'). The contacting in step b') takes place preferably at a temperature in the range from 10 to 50° C., preferably from 20 to 40° C., especially preferably from 30 to 35° C. Preferably the contacting in step b') takes place over a period of 0.5 to 10 h; preferably 1 to 5 h; especially preferably from 1 to 3 h.

Step b') preferably comprises the contacting of the aqueous suspension comprising at least one (preferably precisely one) microorganism selected from *Pseudomonas aeruginosa* (*P. aeruginosa*), *Escherichia coli* (*E. coli*), *Staphylococcus aureus* (*S. aureus*), *Staphylococcus epidermidis* (*S. epidermidis*) and *Candida albicans* (*C. albicans*) in isotonic (physiological) saline solution, the optical density of the aqueous suspension having a value in the range from 0.8 to 1.5, with the solid substrate, preferably at a temperature in the range from 10 to 50° C., preferably from 20 to 40° C., especially preferably at 30 to 35° C., over a period of 0.5 to 10 h; preferably 1 to 5 h; especially preferably from 1 to 3 h.

The contacting in step b') takes place preferably in a microtiter plate.

After the adhesion phase, as for example after step b') and/or c'), the planktonic microorganisms (i.e., the microorganisms which have not adhered) may optionally be determined in the aqueous suspension. This may serve in particular for monitoring, more particularly for monitoring or quantifying the amount of microorganisms which were available for adhesion to the substrate. The amount of the planktonic cells after the adhesion phase, more particularly after step c'), is ascertained preferably by determining the optical density of the aqueous suspension. The optical density is measured typically at a wavelength of about 595 nm. The optical densities (OD) measured may be correlated by calibration with the number of colony-forming units (CFU).

The method of the invention for quantitative determination of bacterial adhesion comprises the parting of the solid substrate F from the supernatant suspension and washing of the substrate (step c').

More particularly step c') comprises the removal of the solid substrate from the aqueous suspension and the washing of the substrate with a sterile aqueous medium, more particularly with an aqueous medium as described above in connection with step a'). Washing may typically be repeated 1 to 10 times, preferably 1 to 5 times, preferably 1 to 3 times.

The washing of the substrate in step c') may take place in particular in a microtiter plate.

The method of the invention for quantitative determination of bacterial adhesion comprises the removal of the adhered microorganisms from the solid substrate by exposure to shearing and/or ultrasound and/or enzymes (step d').

In one preferred embodiment, the adhered microorganisms are removed from the solid substrate in step d' by treating the substrate in a vortex and/or with ultrasound. It is possible to combine the stated mechanical methods with an enzyme treatment.

In particular, step d') comprises the contacting of the washed substrate obtained from step c') with an aqueous medium, preferably with an aqueous medium as described above in connection with step a'), and the removing of the adhered microorganisms from the solid substrate by exposure to shearing and/or ultrasound and/or enzymes.

The removing of the adhered microorganisms in step d') takes place preferably in a microtiter plate. The solid substrate obtained from step c') is preferably admixed in a microtiter plate with a sterile aqueous medium, preferably with isotonic saline solution; the microtiter plate is sealed and is treated by exposure to shearing and/or ultrasound and/or enzymes, preferably by exposure to shearing and/or ultrasound. Accordingly, in particular, after step d') an aqueous suspension is obtained which comprises the microorganisms removed.

With regard to the aqueous medium, the preferred embodiments identified under step a') are valid analogously.

The method of the invention for quantitative determination of bacterial adhesion comprises the determining of the amount of microorganisms removed (step e').

Step e'), before the determination of the amount of microorganisms removed, preferably comprises the removing of the solid substrate after step d') from the aqueous suspension which comprises the microorganisms removed.

In particular the invention relates to a method for the quantitative determination of the adhesion of microorganisms as described above, the amount of microorganisms removed being determined in step e') by means of fluorescence measurement, bioluminescence measurement, protein assay or optical density proliferation assay. The amount of microorganisms removed may be reported, in particular, directly in the measured relative unit (e.g., in relative fluorescence units (RFU)) or through the number of colony-forming units (CFU). The number of colony-forming units (CFU) may be obtained in particular by calibration of the measurement method.

In particular, the amount of microorganisms removed in step e') may be determined by staining microorganisms with a fluorescent dye, more particularly with Syto9, and then carrying out evaluation via a fluorescence measurement. The evaluation takes place preferably in a microplate reader. A further possibility is to determine the amount of microorganisms removed by means of staining with a bioluminescent dye (e.g., BacTiterGlo) and bioluminescence measurement, by means of protein assay (e.g., BCA assay, Bradford assay), or by means of optical density proliferation assay. The determination of the amount of microorganisms removed in step e') takes place preferably in a microtiter plate. Preferably steps d') and e') take place in a microtiter plate, with step e') comprising the following steps: removal of the solid substrate from the aqueous suspension, which comprises the removed microorganisms, from the wells of the microtiter plate, addition of a fluorescent dye, more particularly Syto9, and evaluation by means of fluorescence measurement, typically in a microplate reader.

The invention relates preferably to a method for the quantitative determination of the adhesion of microorganisms to a solid substrate, this being a coated substrate, and the amount of microorganisms removed, as determined in step e'), is placed in relation to the amount of microorganisms removed, based on the respective uncoated substrate. Here it is possible in particular to determine the antiadhesive effect of the coating by means of the reduction in adhered microorganisms in relation to the respective uncoated substrate. With preference it is possible to place in relation the corresponding relative, quantitative units (e.g., relative fluorescence units) measured in step e'), in accordance with the following equation:

$$\text{Reduction in adhered bacteria}[\%]=[(RFU_{uc}-RFU_{c})/RFU_{uc}]*100$$

where
$RFU_{uc}$=relative fluorescence units of the removed bacteria of the uncoated substrate
$RFU_{c}$=relative fluorescence units of the removed bacteria of the coated substrate In one preferred embodiment, the invention relates to the above-described method for the quantitative determination of the adhesion of microorganisms to a solid substrate, where at least one of steps a') to e') is carried out wholly or partly in a microtiter plate. Preferably steps b') and d'), more preferably steps b'), c'), d') and e'), are carried out wholly or partly in a microtiter plate.

The contacting of the aqueous suspension in step b') and the removing of the adhered microorganisms in step d') take place preferably in a microtiter plate. With particular preference the invention relates to the above-described determination method where the contacting in step b'), the removing of the adhered microorganisms in step d') and the determining of the amount of removed microorganisms in step e) are carried out wholly or partly in a microtiter plate. With particular preference the invention relates to the above-described determination method where the contacting in step b'), the washing of the solid substrate in step c'), the removing of the adhered microorganisms in step d') and the determining of the amount of removed microorganisms in step e') are carried out wholly or partly in a microtiter plate.

Typically it is possible to use all known formats, especially the common standardized formats, and forms of microtiter plates. By way of example it is possible to use microtiter plates made of polystyrene, polyvinyl chloride or glass, typically having a well form selected from flat bottom (F bottom), flat bottom with rounded corners (C bottom), conically converging bottom (V bottom) and U-shaped depression (U bottom).

The method of the invention for quantitative determination of the adhesion of microorganisms to a solid substrate may be carried out in particular as a high-throughput process, more particularly as a high-throughput screening process.

The method of the invention for quantitative determination of the adhesion of microorganisms to a solid substrate is preferably carried out as a high-throughput process, more particularly as a high-throughput screening process.

The determination method of the invention comprises in particular, before step a') or b'), the washing and/or sterilizing of the solid substrate.

Moreover, the determination method of the invention is subject to the preferred embodiments described above in relation to microorganisms and fibers and/or fabrics.

The present invention relates, moreover, to a method for finishing fibers and/or fabrics as described above, where the finishing achieves a reduction in the adhesion of microorganisms to the fibers and/or fabrics, and which is combined with the above-described quantitative determination method in order to assess the quality of the finishing.

The finishing of fibers and/or fabrics for the purpose of reducing the adhesion of microorganisms to the fibers and/or fabrics is considered sufficient especially when the adhesion of bacteria is reduced by at least 50% by comparison with an unfinished control, preferably by 60% to 100%.

In this context the present invention relates to a method for finishing fibers and/or fabrics as claimed in claim 1 and as described above, comprising the steps of
  a) providing a composition ZS comprising at least one hydrophilic silane derivative S of the general formula (I) and optionally at least one solvent L;
  b) applying the composition ZS to the fibers and/or fabrics;
  c) optionally washing and/or drying the fibers and/or fabrics,
    where the finishing is directed to reducing the adhesion of microorganisms to the fibers and/or fabrics, and where the method comprises the following additional steps for quantitative determination of the adhesion of microorganisms to the fibers and/or fabrics:
  a'1) preparing an aqueous suspension comprising one or more different microorganisms;
  b'1) contacting the aqueous suspension comprising one or more different microorganisms with the finished fibers and/or fabrics from step b) or c) or with part of the finished fibers and/or fabrics from step b) or c);
  c'1) separating the fibers and/or fabrics from the supernatant suspension and washing the fibers and/or fabrics;
  d'1) removing the adhered microorganisms from the fibers and/or fabrics by exposure to shearing and/or ultrasound and/or enzymes;
  e'1) determining the amount of microorganisms removed.

The particular embodiments in connection with the method for finishing and the method for the quantitative determination of the adhesion of microorganisms are valid as described above in a corresponding way.

Figure 1:
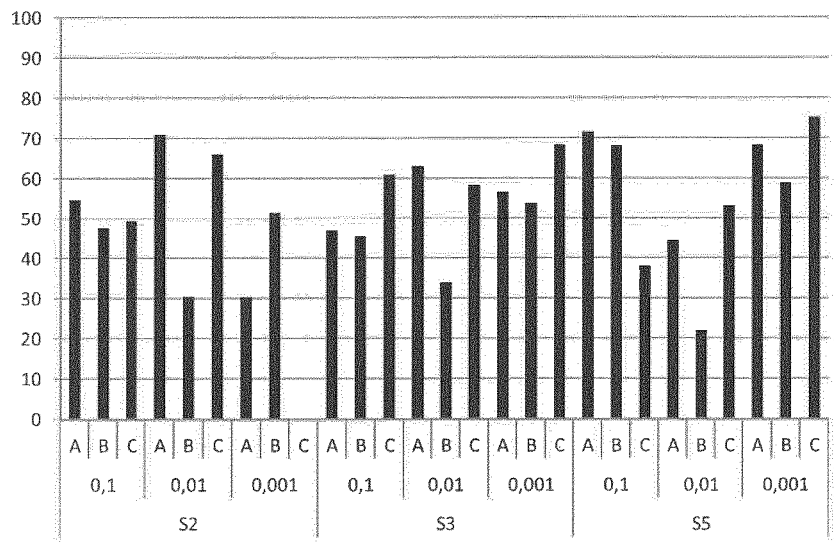
FIG. 1 shows the results relating to the wash stability of the antiadhesive effect (reduction in adhered bacteria in %) with respect to *S. aureus*, concerning a silane derivative coating on polyester fabric samples as per example 3.2.
Figure 2:
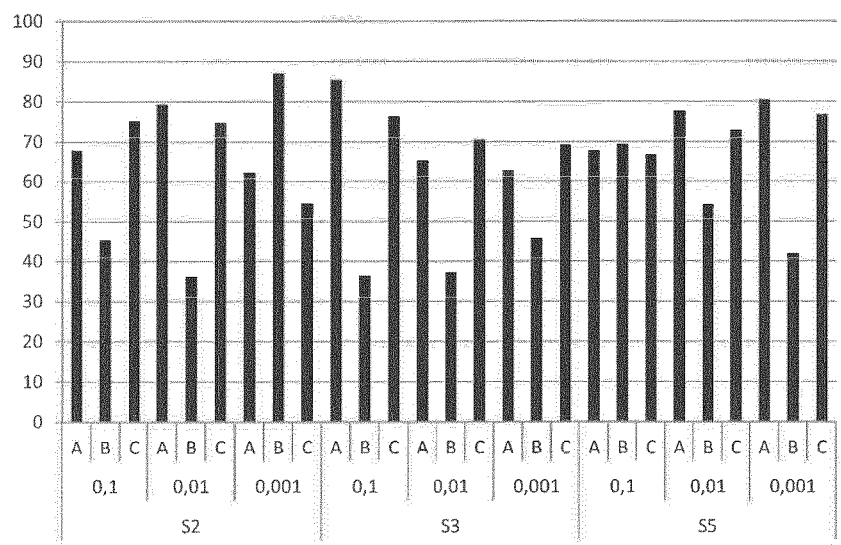
FIG. 2 shows the results relating to the wash stability of the antiadhesive effect (reduction in adhered bacteria in %) with respect to *P. aeruginosa*, concerning a silane derivative coating on polyester fabric samples as per example 3.2.

The abbreviations in FIGS. 1 and 2 are elucidated below:

S2, S3 and S5 denote the corresponding hydrophilic silane derivatives S2, S3 and S5, or polyester fabric samples as per example 3.2 that have been coated with the corresponding silane derivatives;

A, B, and C denote the corresponding pretreatments of the polyester fabric samples (A), (B) and (C) as per example 3.2, i.e., A denotes an unwashed fabric sample; B denotes a fabric sample washed twice at 30° C. just with water, without addition of a detergent; C denotes a fabric sample washed once at 30° C. in accordance with laundry standard EN ISO 6330, method 8A, with addition of an ECE B detergent.

Furthermore, the numbers 0.1; 0.01 and 0.001 denote the corresponding coating concentrations of 0.1 wt %; 0.01 wt % and 0.001 wt % of hydrophilic silane derivative S, based on the weight of the coated textile material.

The invention is elucidated in more detail by the claims and by the examples below:

EXAMPLE 1

Coating of Polyester Fabric Samples

A 10 wt % strength solution of each of the hydrophilic silane derivatives S1 to S4 identified below in methyl triglycol (triethylene glycol monomethyl ether, 2-[2-(2-methoxyethoxy)ethoxy]ethanol was prepared. The hydrophilic silane derivative S5 was dissolved in water to give a 10 wt % strength solution.

Hydrophilic silane derivatives S tested
  S1  methoxy(polyethyleneoxy)propyltrimethoxysilane (9-12 EO units);
    (manufacturer: Gelest, SIM 6492 72)
  S2  bis[3-(triethoxysilylpropoxy)-2-hydroxypropoxy)] polyethylene oxide (5-10 EO units);
    (manufacturer: Gelest, SIB 1824.2)
  S3  N-(triethoxysilylpropyl)-O-polyethylene oxide-urethane, (4-6 EO units);
    (manufacturer: Gelest, SIT 8192.0)
  S4  N-(triethoxysilylpropyl)gluconamide (50% strength solution in ethanol)
    (manufacturer: Gelest, SIT 8189.0)
  S5  N-(trimethoxysilylpropyl)ethylenediaminetriacetyl acid, trisodium salt (45% strength solution in water)
    (manufacturer: Gelest, SIT 8402.0)

The structural formulae of the hydrophilic silane derivatives S1 to S5 are indicated above in the formulae (S1) to (S5).

The above-described solutions (compositions ZS) were applied by a padding method to polyester fabric samples to give application concentrations on the fabric of 0.1 wt %, 0.01 wt % or 0.001 wt % of hydrophilic silane derivative S, based on the total amount of the coated fabric.

In an alternative procedure, the commercial products identified above were applied directly by a padding method to polyester fabric samples to give application concentrations on the fabric of 0.1 wt %, 0.01 wt % or 0.001 wt % of hydrophilic silane derivative S, based on the total amount of the coated fabric.

EXAMPLE 2

Method for the Quantitative Determination of the Adhesion of Microorganisms to Fabrics (Syto9 Assay)

2.1 Production of the Fabric Titer Plates

Circular fabric samples with a diameter of 0.6 cm were punched from coated and uncoated cotton and polyester fabrics. The fabric samples were fixed to a microtiter plate. The fabric samples were washed with acetone and sterilized with UV light for 60 minutes.

2.2 Bacterial Culture and Bacterial Propagation

Model microorganisms used were various gram-positive and gram-negative bacteria and yeasts, more particularly *Pseudomonas aeruginosa* (*P. aeruginosa*), *Escherichia coli* (*E. coli*), *Staphylococcus aureus* (*S. aureus*), *Staphylococcus epidermidis* (*S. epidermidis*) and *Candida albicans* (*C. albicans*).

The strains were coated fresh from glycerol bacterial cultures onto tryptic soy agar (TSA). Incubation took place overnight at 33° C. The nutrient medium prepared was a tryptic soy broth (TSB), with 30% of the amount recommended by the manufacturer, supplemented with 0.25% of glucose. The nutrient medium had a pH of 7 to 7.2. The nutrient medium was inoculated with the bacterial cultures and after inoculation was cultivated overnight at 37° C. and 160 rpm.

The resulting overnight cultures were centrifuged at 8500 g for 15 minutes and washed with 50 ml of isotonic saline solution (0.9 wt %). Bacterial suspensions in isotonic saline solutions were prepared. The optical density of the various bacterial suspensions was determined at 595 nm and adjusted to a level of about 1.2.

2.3 Calibration

In order to be able to correlate the colony-forming units (CFU) and the relative fluorescence units (RFU) in a standard plot, dilution series of the various microorganisms with five-fold dilution were prepared (80 m isotonic saline solution and 20 m microorganism solution). Drops each of 5 µl of the diluted solutions were applied dropwise to three different agar plates (nutrient agar, plate count agar, and tryptic soy agar). The agar plates were incubated with rotation overnight at 33° C. The colony-forming unit count (CFU/ml) was determined on the following day.

In the case of staining with Syto9 (Life Sciences), the same dilution series were prepared for the same time in a black polystyrene plate.

2.4 Biofilm Formation

50 µl of the final microorganism suspension in isotonic saline solution (0.9 wt %) prepared as described under 2.2 were added to the coated and uncoated fabric samples fixed on the microtiter plate (see 2.1). The microtiter plates were closed and sealed off with Parafilm. The microtiter plates were placed in an antievaporation box and incubated at 33° C. for 2 h and at 40 rpm. The expected colony-forming unit count (CFU) of the inoculum at the start was $10^6$-$10^7$ CFU/ml.

After the biofilm had formed, the planktonic cells were removed and used as a sample for determining the optical density at 595 nm. For this purpose, the samples were made up to a volume of 150 µl, and 100 µl were withdrawn for the optical density determination in a photometer. The optical density of the corresponding control solution with sterile isotonic saline solution was subtracted from the optical densities found. Through the determination of the planktonic cells after the formation of biofilm, the amount of bacteria available for adhesion was monitored.

The fabric samples and the resulting biofilm were washed three times with 200 to 300 µl of isotonic saline solution.

2.5 Mechanical or Enzymatic Removal of the Adhered Microorganisms

The fabric samples obtained under 2.4 (after formation of biofilm) were placed together with 100 µl of isotonic saline solution into wells of a 96-well microtiter plate.

Investigations into the removal of the adhered microorganisms from the fabric surfaces were carried out with vortexing, ultrasound, with enzymatic treatment, or with combinations thereof. Treatment in the vortex amounted to 5 minutes and was performed horizontally. The ultrasound treatment was carried out in an ultrasound bath for 5 minutes. For the enzymatic removal, the fabric samples were treated with enzymes, such as trypsin or a mixture of different enzymes, for example, during incubation at 37° C. for 1 hour.

Following removal of the adhered bacteria, the fabric samples were removed from the microtiter plates.

The number of removed bacteria in the resulting suspension was determined by staining with Syto9 and fluorescence measurement (fluorescence filter with excitation at 485/20 nm and emission at 528/20 nm) or by staining with BacTiterGlo and bioluminescence measurement. Furthermore, it is possible to determine the number of adhered and removed microorganisms by means of protein assay (e.g., BCA assay, Bradford Assay) or optical density proliferation assay.

The relative variables (e.g., fluorescence units (RFU)) concerning the coated and uncoated fabrics were compared, allowing the reduction in adhered bacteria in % to be determined in accordance with the following formula:

Reduction in adhered bacteria[%]=[(RFU$_{uc}$−RFU$_{c}$)/ RFU$_{uc}$]*100 where

RFU$_{uc}$=relative fluorescence units of the removed bacteria of the uncoated substrate RFU$_{c}$=relative fluorescence units of the removed bacteria of the coated substrate The statistical significance of each data series was ascertained. The relative measurement units (e.g., relative fluorescence units (RFU)) can be correlated with the aid of calibration plots (see 2.3) to the colony-forming units per ml (CFU/ml).

EXAMPLE 3

Investigation of the Finished Polyester Fabric Samples 3.1 Determinations of the Antiadhesive Effect with Respect to Various Microorganisms As described in example 1, polyester fabric samples were each finished with a hydrophilic silane derivative S1 to S5, to give application concentrations on the fabric of 0.1 wt % (hydrophilic silane derivative S, based on total amount of coated fabric). The commercial products described in example 1 were applied directly by a padding method to polyester fabric samples.

Bacterial adhesion to the polyester fabric samples was investigated using the microtiter plate Syto9 assay, as described in example 2.

For this purpose, polyester fabric samples with a diameter of 0.6 cm were punched out and transferred to a 96-well microtiter plate. The adhesion of S. aureus DSMZ 20231 and P. aeruginosa DSMZ 1117—as representative examples of gram-positive and gram-negative bacteria—was determined as described in example 2, with the adhered bacteria having been removed from the fabric samples by treatment in a vortex. The quantitative determination of the removed bacteria was accomplished by staining with Syto9 and fluorescence measurement (microtiter plate-Syto9 assay). Normal saline solution was used as a sterile control. The experiments were repeated twice independently of one another.

The results in relation to the coating on PES (polyester) fabrics are shown in table 1 below.

TABLE 1

Results relating to the reduction in bacterial adhesion to polyester fabric samples

| No. | Silane derivative S | Reduction in adhered bacteria [%] | |
|---|---|---|---|
| | | S. aureus | P. aeruginosa |
| 1 | S1 | 34 | 41 |
| 2 | S2 | 85 | 64 |

TABLE 1-continued

Results relating to the reduction in bacterial adhesion
to polyester fabric samples

| No. | Silane derivative S | Reduction in adhered bacteria [%] | |
|---|---|---|---|
| | | S. aureus | P. aeruginosa |
| 3 | S3 | 55 | 48 |
| 4 | S4 | 58 | 57 |
| 5 | S5 | 46 | 17 |

The reduction in the adhesion of the two microorganisms was calculated according to the formula given under 2.5. It was shown that polyester fabrics can be successfully coated with the hydrophilic silane derivatives S1 to S5 described, and that these coated fabrics exhibit an up to 85% reduced adhesion of bacteria relative to the uncoated fabrics.

3.2 Investigation of the Wash Stability of the Antiadhesive Coating

Polyester fabric samples were coated with the hydrophilic silane derivatives S2, S3 and S5, as described in example 1, by the application in each case of a 10 wt % strength solution of the silane derivative, as described in example 1, to polyester fabric samples by a padding method.

Fabrics were investigated in each case with coating concentrations of 0.1 wt %; 0.01 wt % and 0.001 wt % of hydrophilic silane derivative, based on the weight of the coated textile material.

The fabric samples were investigated for the wash stability of the antiadhesive effect of the silane coating. The antiadhesive effect was determined by means of the Syto9-microtiter plate assay described in example 3, in a 96-well microtiter plate. Here, separately in each case, the adhesion of the two strains S. aureus and P. aeruginosa to the various fabric samples was assessed.

The antiadhesive effect was determined in each case on fabric samples with the following pretreatments (A), (B) and (C):

(A) on an unwashed fabric sample;
(B) on a fabric sample washed twice at 30° C. only with water, without addition of a detergent;
(C) on a fabric sample washed once at 30° C. in accordance with laundering standard EN ISO 6330, method 8A, with addition of an ECE B detergent.

For each combination, two independent experiments were conducted in each case, in order to obtain information on the reliability of the results.

The results are summarized in tables 2 (testing with respect to S. aureus) and 3 (testing with respect to P. aeruginosa) below. The reduction in the adhesion of the two microorganisms is indicated in each case in %, based on the adhesion to uncoated fabric samples.

The wash stability results are also shown in graph form in FIGS. 1 and 2. FIG. 1 shows the results of table 2 for the wash stability of the antiadhesive effect (reduction in adhered bacteria in %) with respect to S. aureus in relation to a silane derivative coating on polyester fabric samples. FIG. 2 shows the results of table 3 for the wash stability of the antiadhesive effect (reduction in adhered bacteria in %) with respect to P. aeruginosa in relation to a silane derivative coating on polyester fabric samples.

It was found that the maximum reduction in bacterial adhesion of about 40% to 60% is retained under the laundering conditions for all samples investigated. It was shown that the antiadhesive coating of the invention has a high wash stability.

TABLE 2

Wash stability of the antiadhesive effect with respect to S. aureus,
polyester fabric samples, tested using the Syto9 assay

| No. | Silane derivative | Coating concentration [%] | Wash pretreatment | Reduction in adhered bacteria [%] |
|---|---|---|---|---|
| 1 | S2 | 0.1 | (A) | 55 |
| 2 | | | (B) | 48 |
| 3 | | | (C) | 49 |
| 4 | | 0.01 | (A) | 71 |
| 5 | | | (B) | 31 |
| 6 | | | (C) | 66 |
| 7 | | 0.001 | (A) | 30 |
| 8 | | | (B) | 52 |
| 9 | | | (C) | — |
| 10 | S3 | 0.1 | (A) | 47 |
| 11 | | | (B) | 46 |
| 12 | | | (C) | 61 |
| 13 | | 0.01 | (A) | 63 |
| 14 | | | (B) | 34 |
| 15 | | | (C) | 58 |
| 16 | | 0.001 | (A) | 57 |
| 17 | | | (B) | 54 |
| 18 | | | (C) | 69 |
| 19 | S5 | 0.1 | (A) | 72 |
| 20 | | | (B) | 68 |
| 21 | | | (C) | 38 |
| 22 | | 0.01 | (A) | 44 |
| 23 | | | (B) | 22 |
| 24 | | | (C) | 53 |
| 25 | | 0.001 | (A) | 69 |
| 26 | | | (B) | 59 |
| 27 | | | (C) | 75 |

TABLE 3

Wash stability of the antiadhesive effect with respect to P. aeruginosa,
polyester fabric samples, tested using the Syto9-microtiter plate assay

| No. | Silane derivative | Coating concentration [%] | Wash pretreatment | Reduction in adhered bacteria [%] |
|---|---|---|---|---|
| 1 | S2 | 0.1 | (A) | 68 |
| 2 | | | (B) | 45 |
| 3 | | | (C) | 75 |
| 4 | | 0.01 | (A) | 79 |
| 5 | | | (B) | 36 |
| 6 | | | (C) | 75 |
| 7 | | 0.001 | (A) | 62 |
| 8 | | | (B) | 87 |
| 9 | | | (C) | 55 |
| 10 | S3 | 0.1 | (A) | 85 |
| 11 | | | (B) | 36 |
| 12 | | | (C) | 76 |
| 13 | | 0.01 | (A) | 65 |
| 14 | | | (B) | 37 |
| 15 | | | (C) | 71 |
| 16 | | 0.001 | (A) | 63 |
| 17 | | | (B) | 46 |
| 18 | | | (C) | 69 |
| 19 | S5 | 0.1 | (A) | 68 |
| 20 | | | (B) | 69 |
| 21 | | | (C) | 67 |
| 22 | | 0.01 | (A) | 78 |
| 23 | | | (B) | 54 |
| 24 | | | (C) | 73 |
| 25 | | 0.001 | (A) | 81 |
| 26 | | | (B) | 42 |
| 27 | | | (C) | 77 |

3.3 Investigation of the Antimicrobial Effect of the Coated Fabrics

The antimicrobial activity of the coated fabric samples was investigated, in a determination of polyester fabric samples, each coated with a silane derivative S1 to S5, with the aid of the ISO-standardized method as per JIS L 1902, with respect to *Staphylococcus aureus*.

The procedure here is that the fabric sample was inoculated with a defined amount of a microbial suspension (inoculum). Test specimens with a weight of approximately 0.4 g were investigated in a triplicate determination.

The inoculated fabric sample was incubated in a closed system at 37° C. over a period of 18 hours. Following incubation, the bacteria of a defined amount of a dilution solution were recorded. The difference in the bacterial count of the fabric sample at 0 hours in comparison to the fabric sample after 18 hours served as a basis for evaluation. The antimicrobial activity is reported as a logarithmic or percentage value. Here, a reduction in the microbe count of 0% corresponds to inadequate antimicrobial action, a microbe reduction in the range from 0.1 to less than 90% to an inadequate antibacterial action, and a microbe reduction of greater than 90% to a good antibacterial action.

The results relating to the antimicrobial action of the coated fabrics are summarized in table 4 below.

It was found that the coated polyester fabrics exhibit as good as no antimicrobial activity with respect to *Staphylococcus aureus*, with values below log 1 being rated as "no effect".

TABLE 4

Antimicrobial activity on polyester fabric samples

| Silane derivative | Coating concentration [%, based on fabric] | Antimicrobial activity[log] | | |
|---|---|---|---|---|
| | | Unwashed | Washed twice with water | Washed once at 30° C., without detergent |
| untreated | — | −0.5 | −0.1 | −0.5 |
| S2 | 0.1 | −0.2 | 0.00 | −0.4 |
| | 0.01 | −0.4 | 0.1 | −0.6 |
| | 0.001 | 0.2 | 0.1 | −0.1 |
| S3 | 0.1 | 0.0 | 0.3 | −0.4 |
| | 0.01 | −0.1 | 0.8 | −0.1 |
| | 0.001 | −0.5 | −0.3 | −0.8 |
| S5 | 0.1 | −0.5 | −0.4 | −0.6 |
| | 0.01 | −0.3 | −0.2 | −0.6 |
| | 0.001 | 0.5 | 0.9 | −0.3 |

EXAMPLE 4

Investigations on the Adhesion of Microorganisms to a Glass Surface 4.1 Production of the Coated Glass Samples Silane derivatives S1, S3, S4 and S5 as identified above in example 1 were used to produce coatings on glass slides. As a control (comparison sample) K, an uncoated glass slide cleaned with isopropanol was used.

For the coating of the slides they were immersed for 60 seconds into a 0.1% strength solution of the corresponding silane derivative in ethanol/water as solvent with a water fraction of 5%. The solutions had been adjusted with acetic acid beforehand to a pH in the range from 4 to 5. The wetted slides were subsequently dried at 160° C. for 1 hour.

4.2 Determination of the Bacterial Adhesion Via Fluorescence Microscopy

The slides wetted with the bacterial suspension were analyzed by microscope to determine the adhering bacteria. For this purpose, the test culture itself was admixed with a fluorescent dye, which labels the adhering bacteria and hence labels them with unambiguous identifiability on the sample surface. The fluorescent dye used was DAPI (4',6-diamidine-2-phenylindole), which binds to DNA and fluoresces under UV excitation. In order to determine the adhesion characteristics, the cell counts per cm$^2$ were ascertained in 30 measuring windows, and the adhesion pattern was evaluated. Cell attachment was evaluated on an Olympus IX 51 using the Labflow AnalySIS image processing program.

Bacterial suspensions produced and used were suspensions of test cultures of the strains *Staphylococcus aureus* and *Escherichia coli*. The concentration of the bacterial suspension was 10$^9$ microbes/ml.

The results of these measurements are summarized in table 5 below.

TABLE 5

Results of microscopic evaluation - cell counts ascertained per cm$^2$

| Silane derivative | Cell count [1/cm$^2$] | | Reduction in cell count relative to control [%] | |
|---|---|---|---|---|
| | S. aureus | E. coli | S. aureus | E. coli |
| S1 | 110 000 | 296 000 | 76 | 63 |
| S3 | 77 000 | 233 000 | 83 | 71 |
| S4 | 383 000 | 389 000 | 17 | 51 |
| S5 | 219 000 | 306 000 | 52 | 61 |
| K (control) | 460 000 | 791 000 | — | — |

All samples show much less of an adhesion by bacteria in comparison to the glass control, with both general and species-specific trends being discernible.

In the case of adhesion experiments with *S. aureus* it is noted that there is a wide scatter of the results. For instance, with sample S4, only 16% reduction in adhesion relative to the control is ascertained, whereas the sample S3 shows a reduction of 83%. Very good results were achieved in this experiment by specimens S1 and S3. In the case of microscopic inspection, the coated surfaces S4, like the other specimens, showed only a few grapelike assemblies of *S. aureus*, which represents the typical cell morphology of the Staphylococci. The control, in contrast, in part showed a congregation of the cells to form very large assemblies, which were not observed on the coated specimens.

The cell adhesions in the case of *E. coli* were comparatively close to one another for all of the samples and gave a reduction in cell count by at least 50 percent relative to the control K (uncoated glass slide). Microscope inspection showed that in the case of the adhesion of *E. coli* there was predominantly adhesion of individual cells, with stringlike assemblies being observed sporadically.

In both series of tests, very good results were achievable in particular for the glass surfaces coated with silane derivatives S3 and S1.

The invention claimed is:

1. A method for finishing fibers and/or fabrics, comprising the steps of
a) providing a composition ZS comprising at least one hydrophilic silane derivative S of the general formula (I)

where
R$^1$, R$^2$ and R$^3$ independently of one another are H or C$_1$-C$_6$ alkyl;
a is an integer from 1 to 10;
R$^4$ is selected from:

i) 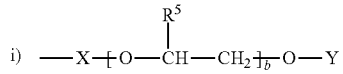

where
X is a bond, —O—T—, —O—T—CH(OH)—, —O—T—CH(OH)—T'—, —O—C(=O)— or —O—C(=O)—T—, where T and T' independently of one another are selected from C$_{1-12}$ alkylene;
R$^5$ is independently at each occurrence H or C$_{1-6}$ alkyl;
Y is H; C$_{1-12}$ alkyl; C$_{1-12}$ hydroxyalkyl, C$_{1-12}$ haloalkyl, C$_{7-20}$ arylalkyl, —C(=O)(C$_{1-12}$ alkyl); —(CH$_2$)$_a$—Si(OR$^1$)(OR$^2$)(OR$^3$), —T—O—(CH$_2$)$_a$—Si(OR$^1$)(OR$^2$)(OR$^3$); —T—CH(OH)—O—(CH$_2$)$_a$—Si(OR$^1$)(OR$^2$)(OR$^3$), or —T—CH(OH)-T'—O—(CH$_2$)$_a$—Si(OR$^1$)(OR$^2$)(OR$^3$) where R$^1$, R$^2$, R$^3$, T, T' and a are as defined above;
b is a number from 0 to 20;
or

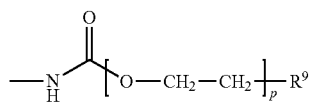

(xv)

where p=1 to 20 and R$^9$ is selected from —OH, —OCH$_3$, —OCH$_2$CH$_3$ and —NH$_2$;
and optionally at least one solvent L;
b) applying the composition ZS to the fibers and/or fabrics;
c) optionally washing and/or drying the fibers and/or fabrics.

2. The method as claimed in claim 1 characterized in that R$^1$, R$^2$ and R$^3$ independently of one another are methyl or ethyl and a is 3.

3. The method as claimed in claim 1, characterized in that R$^4$ is a group selected from:

 (x)

where b=2 to 20 and Y is selected from H and C$_1$-C$_6$ alkyl;

 (xi)

where Y is selected from H, C$_{1-6}$ alkyl and —C(=O)(C$_{1-12}$ alkyl);

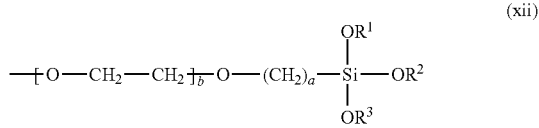 (xii)

where a is 2 to 6, b is 2 to 10, and R$^1$, R$^2$ and R$^3$ are independently of one another methyl or ethyl;

where a is 2 to 6, b is 2 to 20 and R$^1$, R$^2$ and R$^3$ are independently of one another methyl or ethyl.

4. The method as claimed in claim 1, characterized in that the composition ZS comprises a solvent L selected from the group consisting of water, mono- and polyhydric C1-6 alcohols, glycol, glycol derivatives, polyglycols, polyglycol ethers, ethers and mixtures thereof.

5. The method as claimed in claim 1, characterized in that the composition ZS comprises at least one solvent L selected from the group consisting of water, methyl triglycol, ethylene glycol, polyethylene glycol, propylene glycol, polypropylene glycol, propylene glycol monomethyl ether, propylene glycol dimethyl ether, propylene glycol monoethyl ether, propylene glycol diethyl ether, methanol, ethanol, propanol and butanol.

6. The method as claimed in claim 1, characterized in that the composition ZS comprises 0.0001 to 10 wt %, based on the overall composition ZS, of the at least one hydrophilic silane derivative S.

7. The method as claimed in claim 1, characterized in that the composition ZS is applied in step b by pad mangle methods, foam application, spraying methods, coating or an exhaust method.

8. The method as claimed in claim 1, characterized in that the fibers and/or fabrics comprise synthetic fibers.

9. The method for finishing fibers and/or fabrics as claimed in claim 1, where the finishing is directed to reducing the accretion of microorganisms onto the fibers and/or fabrics, and where the method comprises the following additional steps for quantitative determination of the accretion of the microorganisms onto the fibers and/or fabrics:

a'1) preparing an aqueous suspension comprising one or more different microorganisms;

b'1) contacting the aqueous suspension comprising one or more different microorganisms with the finished fibers and/or fabrics from step b) or c) or with part of the finished fibers and/or fabrics from step b) or c);

c'1) separating the fibers and/or fabrics from the supernatant suspension and washing the fibers and/or fabrics;

d'1) removing the accreted microorganisms from the fibers and/or fabrics by exposure to shearing and/or ultrasound and/or enzymes;

e'1) determining the amount of microorganisms removed.

10. A method for coating a solid substrate with a composition comprising at least one hydrophilic silane derivative S of the general formula (I) as in claim 1, wherein the accretion of microorganisms onto the solid substrate is reduced.

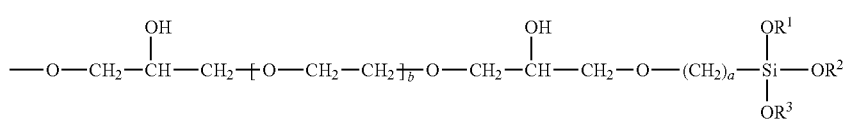 (xiii)

11. The method as claimed in claim 10, characterized in that the solid substrate is a substrate selected from glass, ceramic, plastic, metal, fibers and fabrics.

* * * * *